United States Patent [19]

Newman

[11] Patent Number: 5,146,289
[45] Date of Patent: Sep. 8, 1992

[54] NONDESTRUCTIVE TESTING USING AIR-COUPLED ACOUSTIC EXCITATION

[75] Inventor: John W. Newman, Berwyn, Pa.

[73] Assignee: Laser Technology, Inc., Norristown, Pa.

[21] Appl. No.: 631,985

[22] Filed: Dec. 21, 1990

[51] Int. Cl.$^5$ .............................................. G01B 9/02
[52] U.S. Cl. .................................. 356/35.5; 356/359; 73/656
[58] Field of Search ...................... 356/360, 35.5, 359; 73/656, 655, 657

[56] References Cited

U.S. PATENT DOCUMENTS

| | | | |
|---|---|---|---|
| 3,645,129 | 2/1972 | Grant | 73/656 |
| 3,828,126 | 8/1974 | Ramsey, Jr. | 73/656 |
| 4,408,881 | 10/1983 | Clarady | 356/347 |

Primary Examiner—Samuel A. Turner
Assistant Examiner—Richard E. Kurtz, II
Attorney, Agent, or Firm—William H. Eilberg

[57] ABSTRACT

An object is tested for defects by interferometry, by comparing images of the object taken under stressed and unstressed conditions. The stress is applied by perturbing the object with acoustic waves, produced by a speaker directed towards the object, without any mechanical coupling to the object. The acoustic energy can be of a single frequency, or it can be distributed over a set of random frequencies (i.e. white noise), or it can be in the form of a signal which is "swept" through a range of frequencies. In the latter case, the results can be stored in a video buffer which records the maximum signal obtained, for each pixel, while the signal is swept through the frequency range. Different defects in the object may resonate at varying frequencies within the given range. By exciting the object at each frequency within the range, and superimposing the maximum signals obtained for each pixel, the resulting image is likely to show all the locations on the object which may be defective. The preferred form of interferometry is electronic shearography, which is particularly suitable for recording interference patterns in a video buffer. The present invention is especially useful in detecting delaminations in bonded articles, and is particularly advantageous in testing large objects.

8 Claims, 2 Drawing Sheets

NONDESTRUCTIVE TESTING USING AIR-COUPLED ACOUSTIC EXCITATION

BACKGROUND OF THE INVENTION

This invention relates to the field of nondestructive testing of objects by interferometry. The invention provides a method and apparatus for perturbing the object being tested, without mechanical coupling between the source of excitation and the object. It is especially useful for testing large objects, and also for testing manufactured articles which may be subject to delamination.

The invention is especially useful in testing so-called "honeycomb" structures used in aircraft. Such structures include a core having cells of hexagonal cross-section (hence the name "honeycomb"), and can be made of metal or ceramic materials. The honeycomb core is typically covered by a "skin" made of aluminum, Fiberglas, paper, graphite, or other material. Also, such honeycombs can include layers of honeycomb cores separated by layers of such skins. The present invention can be used to test such objects for delamination of the skin, and/or disassembly of the honeycomb structure itself.

Nondestructive testing is the detection and analysis of defects in an object, wherein the object is not damaged by the test. Conventional methods of nondestructive testing have included bombarding an object with ultrasonic waves, and detecting the changes in amplitude of the waves as they travel through the object or as they are reflected by a defect within the object. The latter method has the disadvantage that a water medium is generally required to conduct the ultrasonic waves to the object. Therefore, the method requires wetting the object.

Another method of nondestructive testing is radiography, which includes passing x-rays through the object. Radiography is useful in determining whether there is a cavity within the object, but it is not generally useful for detecting delaminations in composite structures or in the honeycomb panels mentioned above. Radiography cannot detect "unbonds" in composite structures unless the x-rays happen to be directed in exactly the correct plane.

Another method of nondestructive testing is shearing interferometry, or "shearography". In shearography, interferograms are formed by superimposing two laterally displaced ("sheared") images of the same object. In shearography, one compares an interferogram, or "shearogram", taken while the object is not stressed with similar interferograms taken while the object is stressed. Examples of methods of shearography are given in U.S. Pat. Nos. 4,139,302 and 4,887,899, the disclosures of which are incorporated herein.

In the prior art, a vacuum is commonly used as the means of stressing the object being tested. A relatively small test object such as a honeycomb panel can be rapidly and reliably deformed with a vacuum, for purposes of nondestructive testing. But if that object is installed on an aircraft, it may be very difficult to remove for testing. In such cases, vacuum stressing is impractical and unsatisfactory.

Another example of the shortcomings of vacuum stressing is in the analysis of the foam insulation on a cryogenic fuel tank of a space vehicle. The size of such an object precludes the use of a vacuum test chamber. Moreover, for soft materials such as foam, vacuum stressing can damage the object being tested. Vacuum stressing is often performed with a vacuum window, which can be a flat piece of clear plastic having a seal around its perimeter, and which, when pressed against the object, forms a vacuum chamber having one side defined by the object. The vacuum window may cause local damage at the point of contact. Also, many large structures used in the aerospace industry are not easily accessible, even when a vacuum window is used. In many cases, an inordinate amount of labor is required to position the nondestructive testing equipment.

It has also been known to perturb an object by vibration. U.S. Pat. No. 4,408,881 describes the vibrational excitation of a test object using a random frequency ("white noise") generator, and using mechanical coupling between the source of excitation and the test object. While the latter technique is useful when it is necessary to detect small delaminations or "unbonds", having a principal dimension of about ⅛ inch or smaller, the technique has the disadvantage that it requires excitation of the entire object. Thus, the greater the weight of the test object, the greater the energy required to vibrate the object.

Another problem with the above-described method is that it is very difficult to design a mechanical coupling device which will uniformly excite a large test object. Test objects having a principal dimension of 10 inches or larger are generally excited more at the point of attachment of the mechanical coupling than at other points. This nonuniformity makes it difficult to interpret the resulting interferogram. Thus, while vibrational excitation by mechanical coupling is useful with small test objects, it cannot be used effectively for determining the mechanical integrity of aircraft or other large structures.

The present invention solves the problem of nondestructively testing a large and heavy object, by providing a method and apparatus for air-coupled acoustic excitation of the object. The invention is especially suitable for detecting delaminations near the surfaces of composite structures. It is also an effective means of testing a large object which is difficult to vibrate, and which cannot be easily mechanically coupled to a testing apparatus.

SUMMARY OF THE INVENTION

According to the invention, a test object is illuminated with coherent radiation, preferably laser light. An interferometer detects images of the object, formed by light reflected from the object. The preferred method of interferometry is shearography, especially electronic shearography, though other interferometric methods, such as holography, can also be used. The purpose of the interferometer is to compare an image of the object, taken when the object is not stressed, with an image taken when the object is perturbed. The object is perturbed by acoustic waves. The object can be excited by using a signal generator and amplifier to drive a speaker positioned near the object. The speaker and the object are not mechanically coupled; the acoustic waves simply travel through the air to the object.

The shearogram, or other interferogram, taken while the object is unstressed, is compared with one or more interferograms taken while the object is stressed. Differences between the interferograms provide information on the condition of the object. In the method known as electronic shearography, the interferograms are compared electronically, and the method has the advantage that results can be displayed in "real time".

The signal generator selected can be one which produces a signal having a single frequency, or it can be one which generates acoustic waves having random frequencies, i.e. "white noise". In the preferred embodiment, the signal generator produces a signal which is "swept" through a range of frequencies. Thus, at each moment in time, the object is bombarded with acoustic waves having a single frequency, this frequency being changed from one moment to the next. The latter method generally provides the most sensitive test, because it insures that the object will be subjected to waves of each frequency within the range. In general, a delamination in the object will resonate at a particular characteristic frequency. The latter method is likely to detect resonances at the various characteristic frequencies.

It is therefore an object of the present invention to provide a method and apparatus for nondestructive testing of an article.

It is another object to provide a method of nondestructive testing which is suitable for use with large and heavy articles.

It is another object to provide a method of nondestructive testing which is suitable for testing an article installed on an aircraft or space vehicle.

It is another object to provide a method of nondestructive testing of articles which cannot be conveniently moved, or of articles which can be conveniently observed from only one side.

It is another object to provide a method of nondestructive testing which minimizes the energy required to perturb the article being tested.

It is another object to provide a method of nondestructively testing a composite structure by locating resonances caused by delaminations in the structure.

It is another object to reduce the cost of nondestructive testing of large structures.

Other objects and advantage of the invention will be apparent to those skilled in the art, from a reading of the following brief description of the drawings, the detailed description of the invention, and the appended claims.

DETAILED DESCRIPTION OF THE INVENTION

Figure 1:
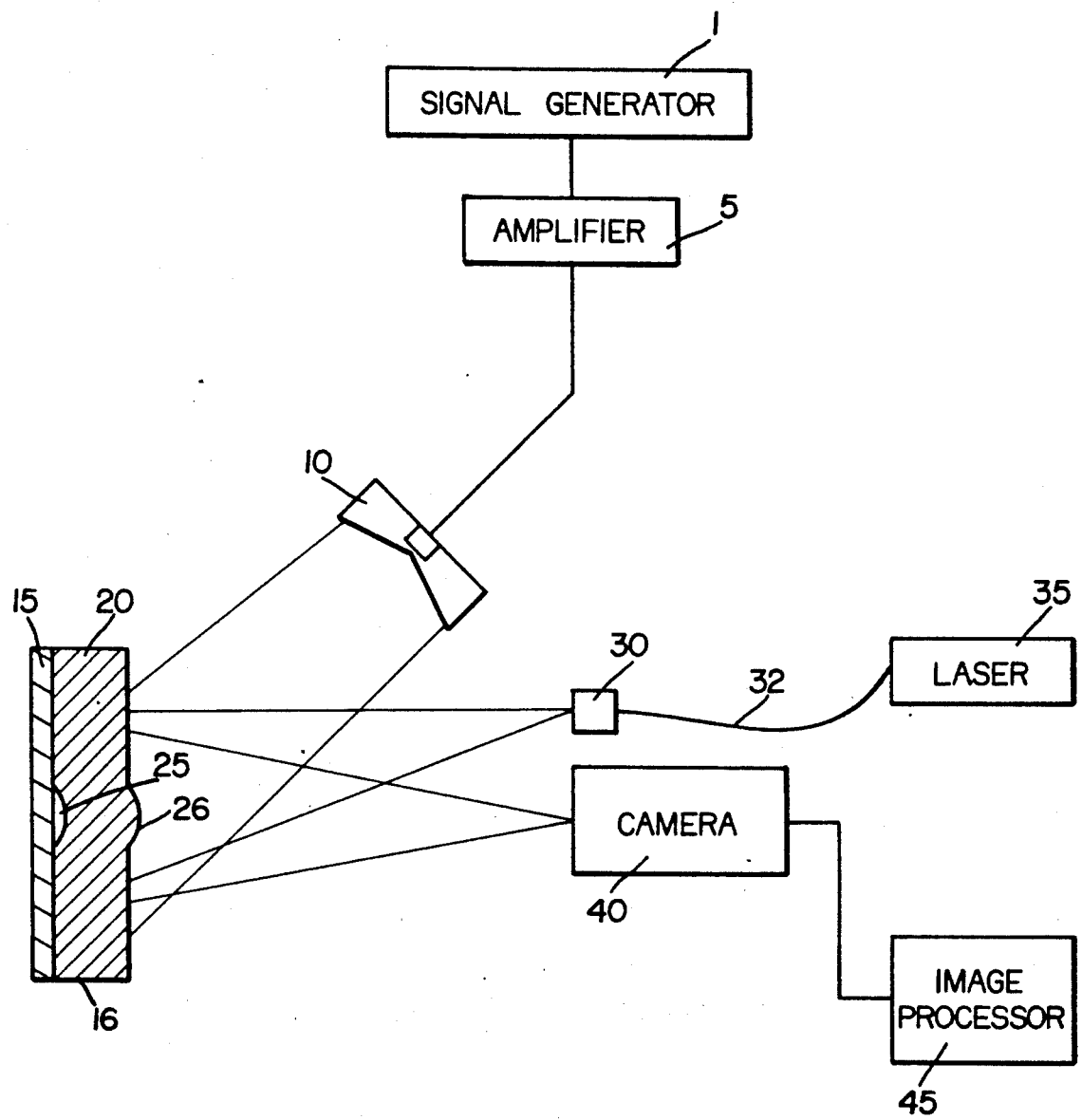
FIG. 1 is a schematic diagram of a first embodiment of the present invention.

FIG. 1 is a schematic diagram of one embodiment of the invention. Signal generator 1 generates a waveform which is amplified in amplifier 5. The amplified signal drives speaker 10, which is positioned near test object 16. The speaker is separated from the object by a gaseous medium, such as air, which will conduct acoustic waves. The test object comprises two bonded materials 15 and 20. In FIG. 1, the object is shown with a delamination, or "unbond", indicated by reference numeral 25. FIG. 1 also shows a bulge 26, in the outer surface of the material 20. The bulge is generally parallel to the unbond, and results from the fact that the material tends not to become compressed when the unbond is created. The unbond and the bulge are exaggerated in the figure, for clarity of illustration. When material 20 is separated from material 15 at the unbond, as shown in FIG. 1, the material 20 will oscillate when excited, in the region of the unbond.

If the object is large and heavy, or if it is mounted on an aircraft and cannot be conveniently moved, it is desirable to perform all the analysis from one side of the object only, i.e. from the side of bulge 26.

In the embodiment of FIG. 1, the means of interferometry is shearography. Shearography is the preferred method of interferometry, for the reasons given above. Shearography camera 40 is directed towards the area on the object which is exposed to acoustic energy. The object is illuminated by laser 35, which is connected by fiber optic cable 32 to fiber optic illuminator 30. The fiber optic illuminator is commercially available, and can be a device such as that sold as Model F-125 by Laser Technology, Inc., of Norristown, Pa. Alternatively, the laser can be aimed directly at the object, without a separate illuminator.

The fiber optic illuminator is positioned to illuminate the object over the field of view of camera 40. The camera contains the optical elements necessary to produce a shearogram. These elements are fully described in the above-cited patents, and are not part of the present invention. The apparatus also includes shearography image processor 45, which can include a computer, or its equivalent, for storing and comparing the shearographic images generated by camera 40. The image processor preferably also includes a video monitor. The image processor operates continuously, and displays, on the monitor, an image which represents the comparison between the most recent interferogram taken of the object, and the initial, or "reference", interferogram. The comparison can be made by simply calculating the difference between interferograms, or by any of the other techniques described in U.S. Pat. No. 4,887,899, or by other means. The difference can be calculated by calculating the difference between two digitized interferograms, i.e. by subtracting corresponding pixels from each other.

In operation, an image buffer, within image processor 45, is cleared and then loaded with the initial, reference interferogram of the test object. The reference interferogram is produced by camera 40, and is obtained without excitation of the object. That is, the reference interferogram represents the object in the unstressed condition. As long as there is no excitation, i.e. while no acoustic energy is coming from the speaker, the video monitor remains black, because there is no change in the object from its initial condition.

When the signal generator and amplifier are activated, the object is perturbed by acoustic energy, and a pattern appears on the video monitor. The pattern represents a comparison of the current image with the reference image. The pattern can be generated by computing the algebraic difference between the current and initial patterns, or by the other methods of comparison described in U.S. Pat. No. 4,887,899, or by other means. The image observed on the monitor is directly related to the modal patterns comprising the response of the object to acoustic excitation. The image thus obtained is "frozen" for further analysis.

In the method described above, a single frequency of acoustic energy is used. The resulting image shows the modes of resonance of defective portions of the object. One sees white patches on the video screen, indicating where the object has moved due to the applied stress. However, in general, the image will not tell a complete story, because it will show only some of the vibrational modes, i.e. those modes which correspond to the frequency of excitation.

The modes of vibration of an object depend on the stiffness of the structure and on its geometry. The vibrational modes for most test objects occur at low frequencies of excitation, in the range of about 10–10,000 Hz. Since defects in an object are generally much smaller than the object itself, these defects resonate at higher frequencies, of the order of about 1,200–20,000 Hz. Thus, by bombarding the object with acoustic waves having frequencies above that which causes a non-defective object to vibrate, one avoids excitation of the inherent structural modes of vibration, and can test for defects with greater accuracy.

As stated above, the use of a single frequency of excitation has the disadvantage that a defect may be missed because the frequency used did not correspond to the resonant frequency of the defect. One way of overcoming this disadvantage is to excite the object with "white noise", i.e. an acoustic wave having a large number of frequency components. A random noise generator is preferably connected to a filter which removes the low-frequency components, so that the white noise is concentrated in the frequency band most likely to correspond with the resonant frequency of a defect.

The patterns obtained using white noise excitation are generally useful for defects which resonate across a relatively broad spectrum. But when the defects are small or the unbonds are relatively tight, excitation with white noise has disadvantages. One problem with white noise is that its energy is distributed across a relatively broad spectrum. Thus, the energy of the acoustic wave for any particular frequency is relatively low. Therefore, the acoustic wave may be insufficient to excite some vibrational modes, and defects in the object may be missed. Another problem is that small or stiff unbonds may have a narrow resonant frequency response curve (i.e. the resonance has a high "Q"), making it less likely that the resonance will be detected by an acoustic wave having a plurality of discrete frequencies.

The above problems with white noise can be overcome by exciting the object with an acoustic wave which is "swept" through a predetermined frequency band. That is, the acoustic wave, at each given moment, is concentrated at essentially one frequency, the frequency being moved from a low value to a high value at a predetermined rate.

The choice of the rate at which the frequency is swept depends on several factors. If the unbonds in the object are expected to be small or stiff, it is preferred to use a lower rate of "sweep", to insure that each unbond has the chance to resonate at its characteristic frequency. Thus, even unbonds that have little difference in stiffness from that of the well-bonded material can be made to resonate at some frequency within the range. However, if the rate of sweep is slow, the persistence of the phosphor in the video monitor may not be sufficient to produce a complete image representing an entire sweep through the frequency range. In the latter case, it may be necessary to store the peak values obtained at each pixel in a video buffer. On the other hand, increasing the frequency sweep rate to approximately one-half or more of the video frame rate obviates the need to use video peak storage capability to view defects in the object, but reduces the chance that each unbond in the object will resonant at each frequency.

If the test object has small or tight unbonds, it is preferably to employ a video peak storage technique, and to sweep the frequency slowly to provide the most sensitive test. Sweeping the frequency over the peak of the frequency response curve will produce a momentary indication on the video monitor. This indication can be stored in a video peak storage unit, which can be a conventional video buffer. Initially, all of the video memory locations are set to "black". Any change in the gray scale level, for a given pixel, in the direction of "white", due to a signal from the interferometer, is stored. For each pixel, the buffer stores the signal of maximum brightness, for any period of time during the test. The contents of the buffer are displayed on the monitor. Each pixel in the resulting pattern therefore represents the maximum value of brightness obtained for that pixel, while the frequency was swept through its range. Thus, small unbonds with a very narrow resonance curve can be detected, and their presence illustrated, in fixed form, on a video image. The operator of the system can thus directly view an image showing flaws beneath the surface of the test object.

Figure 2:
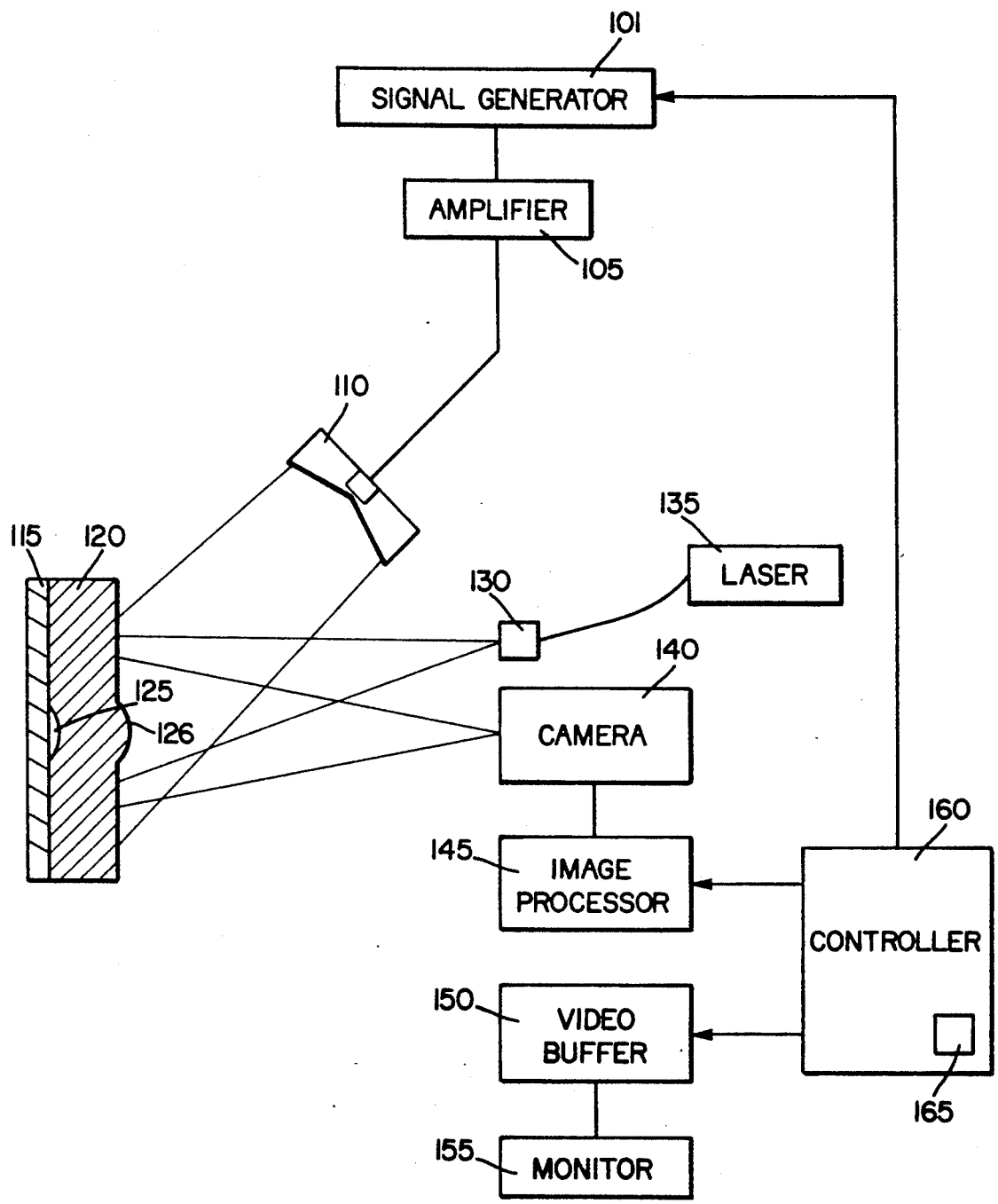
FIG. 2 is a schematic diagram of a second embodiment of the invention, showing an apparatus for storing the maximum signal level observed at each pixel of the image.

FIG. 2 shows an apparatus for practicing the method described above. Signal generator 101 produces a signal which is amplified by amplifier 105, which drives speaker 110. Sound from the speaker perturbs the object which includes materials 115 and 120 which are separated at an unbond 125. The unbond produces bulge 126, similar to bulge 26 of FIG. 1. Laser 135, connected by a fiber optic cable to illuminator 130, illuminates the object, and images of the object are obtained from shearography camera 140. Shearography image processor 145 receives images from camera 140, and is also connected to video buffer 150. The contents of the buffer are viewed on video monitor 155. A logic controller 160 controls the video buffer and the signal generator. Controller 160 can erase the contents of memory in the image processor and video buffer, and also causes the contents of the buffer to be "frozen". Thus, the operator can simply aim the equipment at the object, press a test button 165, and the apparatus will perform the test automatically. The video image of the object, showing any flaws in the object, will appear on the video monitor in a very short time, as determined by the sweep rate and the setting of timing circuits in the logic controller. The timing circuit includes a sequencer that automatically captures the reference image, activates the acoustic excitation, captures the subsequent image(s), etc., thus automating the entire process.

The air-coupled acoustic excitation of the present invention has the advantage that the object being tested is uniformly excited. The method excites only the outer material of a bonded structure, where delaminations are likely to occur. Using air-coupled acoustic excitation therefore eliminates the need to perturb the entire object. This feature is especially advantageous if one wants to excite, say, the nose cone of a solid rocket booster. Such a structure weighs several hundred pounds, and a high-performance shaker to cause the entire structure to vibrate would be prohibitively expensive and impractical. But with air-coupled acoustic stressing, only the thermal insulation coating need be excited. The latter test requires less than 100 watts of power, and the equipment for performing the test is small, light in weight, and relatively inexpensive.

The invention is not limited to use with bonded structures, but can be used in other contexts. For example, the invention can be used to examine a wooden hull of a boat for soft spots. However, the invention is usually not appropriate for detecting bond lines more than about two inches deep within the object. The depth to which the method of the present invention is applicable depends on the nature of the material.

Acoustic coupling is especially desirable when used with a nondestructive testing technique such as shearography. Shearography is inherently sensitive to the derivative of the out-of-plane deformation of the test object. Thus, shearography largely avoids the requirement of vibration isolation that is mandatory with other interferometric techniques such as holography. Shearography is therefore particularly useful for the nondestructive testing of large objects that cannot be isolated from vibration.

While shearography is usually the preferred method of interferometry, the invention can be used with other interferometric techniques, and is not intended to be limited to shearography.

The embodiments described above should not be interpreted to limit the scope of the invention. Many modifications are possible. The type of interferometer can be varied, and the optical apparatus can be changed. For example, the fiber optic cable could be eliminated, and the object could be illuminated directly by the laser. The means of generating acoustic waves can be changed. The video peak storage buffer can be a hardware unit, which is commercially available, or it can be implemented in software. These and other modifications should be deemed within the spirit and scope of the following claims.

What is claimed is:

1. An apparatus for nondestructively testing an object, comprising:
   a) means for reflecting coherent radiation from the object, and for forming an image of the object with the reflected radiation,
   b) means for perturbing the object with acoustic energy, the perturbing means comprising means for generating acoustic energy having a frequency which changes continuously from a first value to a second value, the first and second values being different, the perturbing means being operable while the coherent radiation continues to be reflected from the object, wherein a plurality of images of the object can be formed by the image-forming means while the object is being perturbed,
   c) means for generating a series of composite patterns representing comparisons of images formed while the object is perturbed, with an image formed while the object is not perturbed, wherein each of said composite patterns is stored in a video buffer having a plurality of pixels, and
   d) means for generating an image representing the maximum of all the composite patterns in said series, the latter generating means comprising means for forming a pattern each pixel of which is the pixel of greatest intensity of all corresponding pixels obtained from said composite patterns of said series.

2. The apparatus of claim 1, wherein the perturbing means comprises means for perturbing the object without any mechanical coupling to the object.

3. The apparatus of claim 2, wherein the perturbing means comprises means for directing acoustic energy through a gaseous medium, towards the object.

4. The apparatus of claim 3, wherein the gaseous medium is air.

5. A method of nondestructively testing an object, the method comprising the steps of:
   a) reflecting coherent radiation from the object, and forming an image of the object with the reflected radiation,
   b) perturbing the object by directing acoustic energy towards the object, the acoustic energy having a frequency which changes continuously from a first value to a second value, the first and second values being different, the perturbing step being performed while the coherent radiation continues to be reflected from the object, so as to form a plurality of images of the object while the object is being perturbed, and
   c) forming, for each image formed in step (b), a composite pattern representing the comparison of the image formed in step (a) with an image formed in step (b), wherein each composite pattern is recorded in a video buffer having a plurality of pixels, and
   d) generating an image representing the maximum of all the composite patterns formed in step (c), the generating step including forming a pattern each pixel of which is the pixel of greatest intensity of all corresponding pixels obtained in the patterns of step (c).

6. The method of claim 5, wherein the perturbing step is performed without any mechanical coupling between the source of acoustic energy and the object.

7. The method of claim 6, wherein the perturbing step comprises the step of directing acoustic energy through a gaseous medium, towards the object.

8. The method of claim 7, wherein the gaseous medium is air.

* * * * *